(12) United States Patent
Mungilwar

(10) Patent No.: US 7,190,763 B2
(45) Date of Patent: Mar. 13, 2007

(54) EXPOSURE CALCULATION METHOD AND RADIOGRAPHY SYSTEM

(75) Inventor: Naresh Mungilwar, Bangalore (IN)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 11/017,257

(22) Filed: Dec. 20, 2004

(65) Prior Publication Data
US 2005/0152498 A1    Jul. 14, 2005

(30) Foreign Application Priority Data
Dec. 26, 2003 (JP) .............................. 2003-432791

(51) Int. Cl.
*H05G 1/42* (2006.01)
(52) U.S. Cl. ......................................... 378/97; 378/108
(58) Field of Classification Search ................. 378/64, 378/65, 97, 108, 117, 207
See application file for complete search history.

(56) References Cited

U.S. PATENT DOCUMENTS

| | | | |
|---|---|---|---|
| 4,274,005 A | 6/1981 | Yamamura et al. ............. 378/9 |
| 4,672,648 A | 6/1987 | Mattson et al. ................ 378/4 |
| 4,868,843 A | 9/1989 | Nunan ......................... 378/152 |
| 5,694,449 A | 12/1997 | Aragones ..................... 378/115 |
| 5,982,846 A | 11/1999 | Toth et al. .................... 378/19 |
| 6,249,565 B1 * | 6/2001 | Tarr ............................. 378/65 |
| 6,330,299 B1 * | 12/2001 | Curtis et al. .................. 378/62 |
| 6,466,640 B1 | 10/2002 | Taguchi ....................... 378/15 |

FOREIGN PATENT DOCUMENTS

JP    2003-203797    7/2003

* cited by examiner

*Primary Examiner*—Courtney Thomas
(74) *Attorney, Agent, or Firm*—Carl B. Horton, Esq.; Armstrong Teasdale LLP

(57) ABSTRACT

A method of calculating an exposure a patient receives during radiography includes retrieving a value of a dose rate, which is associated with a value of the tube voltage of an X-ray tube, from a first lookup table that is created in advance, retrieving a value of an area of an X-ray field, which is associated with a value indicating the positions of blades included in a collimator that limits a range of X-ray radiation, from a second lookup table that is created in advance, and calculating the product of the dose rate, the area of the X-ray field, the tube current of said X-ray tube, and an X-irradiation time.

4 Claims, 8 Drawing Sheets

FIG. 5
| Tube voltage | Dose rate (μGy/s) |
|---|---|
| 40 | 23.7 |
| 50 | 42.3 |
| 60 | 61.2 |
| 70 | 81.6 |
| 80 | 102.9 |
| 90 | 125.6 |
| 100 | 149.0 |
| 110 | 173.0 |
FIG. 6
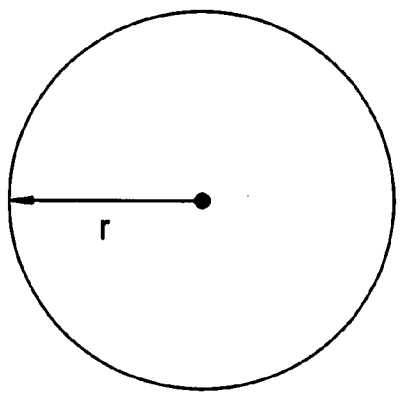
FIG. 7
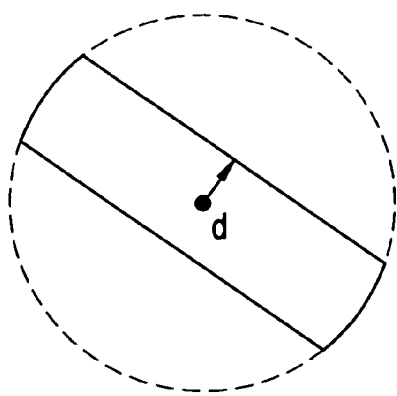

FIG. 8

| Positional value indicating postion of blades of iris (count) | Radius of projection image r (mm) |
|---|---|
| 295 | 7.81 |
| 443 | 5.72 |
| 527 | 4.32 |

FIG. 9

| Positional value indicating positions of blades of shutter (count) | Half width of projection image d (mm) |
|---|---|
| 222 | 14.92 |
| 442 | 7.81 |
| 830 | 0.20 |

EXPOSURE CALCULATION METHOD AND RADIOGRAPHY SYSTEM

CROSS REFERENCE TO RELATED APPLICATIONS

This application claims the benefit of Japanese Application No. 2003-432791 filed Dec. 26, 2003.

BACKGROUND OF THE INVENTION

The present invention relates to an exposure calculation method and a radiography system, and more particularly, to a method of calculating an exposure a patient receives during radiography, and a radiography system including means for calculating the exposure a patient receives during radiography.

A radiography system controls an X-ray exposure so that the X-ray exposure will be set to a predetermined value. The predetermined value is, for example, a minimum necessary exposure. For the control, a dedicated detector is used to detect or monitor an X-ray exposure during radiography. When a value resulting from the temporal integral of the components of a detection signal reaches a predetermined value, X-irradiation is stopped (refer to, for example, Patent Document 1).

[Patent Document 1] U.S. Pat. No. 5,694,449 (third to fifth columns and FIG. 1 to FIG. 4)

According to the above method, the dedicated detector is needed for detecting an X-ray exposure during radiography. Moreover, a signal processing circuit or the like is needed for performing predetermined processing that includes the temporal integral of the components of the detection signal. Therefore, the method is unsuitable for, for example, a mobile radiography system and other radiography systems requested to have a simple configuration, be lightweight, and cost low.

SUMMARY OF THE INVENTION

Therefore, an object of the present invention is to provide a method of calculating an exposure, which a patient receives during radiography, without detecting X-rays, and a radiography system including such exposure calculating means.

(1) According to one aspect of the present invention for accomplishing the above object, there is provided a method of calculating an exposure which a patient receives during radiography. The value of a dose rate associated with the value of a tube voltage of an X-ray tube is retrieved from a first lookup table that is created in advance. The value of the area of an X-ray field associated with the value indicating the positions of blades included in a collimator that limits the range of X-ray radiation is retrieved from a second lookup table that is created in advance. The product of the dose rate, the area of the X-ray field, the tube current of the X-ray tube, and an X-irradiation time is calculated.

(2) According to another aspect of the present invention for accomplishing the above object, there is provided a radiography system including imaging means that images a patient by utilizing X-rays and a detecting means that detects an exposure the patient receives during radiography. The detecting means comprises: a first lookup table in which the values of a dose rate are recorded in association with the values of the tube voltage of an X-ray tube; a second lookup table in which the values of the area of an X-ray field are recorded in association with the values each indicating the positions of blades included in a collimator that limits the range of X-ray radiation; and calculating means for retrieving the value of the dose rate, which is associated with the current value of the tube voltage, from the first lookup table, retrieving the value of the area of the X-ray field, which is associated with the current value indicating the positions of the blades included in the collimator, from the second lookup table, and calculating the product of the dose rate, the area of the X-ray field, the tube current of the X-ray tube, and an X-irradiation time.

Preferably, the first lookup table is created through calibration of the X-ray tube performed using a dosimeter so that the relationship of correspondence between the values of the tube voltage of the X-ray tube and the values of the dose rate can be grasped properly.

Preferably, the second lookup table is created through calibration of the collimator including actual measurement of the area of the X-ray field so that the relationship of correspondence between the values each indicating the positions of the blades included in the collimator and values of the area of the X-ray field can be grasped properly.

Preferably, the relationship of correspondence between the values indicating the positions of blades, which constitute each of an iris diaphragm and a shutter included in the collimator, and the values of the area of the X-ray field is recorded in the second lookup table so that the X-ray field can be adjusted by utilizing the combination of the iris diaphragm and shutter.

According to the present invention, the value of the dose rate associated with the value of the tube voltage of the X-ray tube is retrieved from the first lookup table that is created in advance. The value of the area of the X-ray field associated with the value indicating the positions of the blades included in the collimator that limits the range of X-ray radiation is retrieved from the second lookup table that is created in advance. The product of the dose rate, the area of the X-ray field, the tube current of the X-ray tube, and an X-irradiation time is calculated. Thus, a method of calculating an exposure a patient receives during radiography without detection of X-rays, and a radiography system including such an exposure calculating means are provided.

Further objects and advantages of the present invention will be apparent from the following description of the preferred embodiments of the invention as illustrated in the accompanying drawings.

BRIEF DESCRIPTION OF THE DRAWINGS

FIG. 5 lists the actually measured values of a dose rate.

FIG. 6 shows a projection image of a window of the collimator.

FIG. 7 shows a projection image of another window of the collimator.

FIG. 8 lists the actually measured values of the radius of the projection image.

FIG. 9 lists the actually measured values of the half width of the projection image.

DETAILED DESCRIPTION OF THE INVENTION

Figure 1:
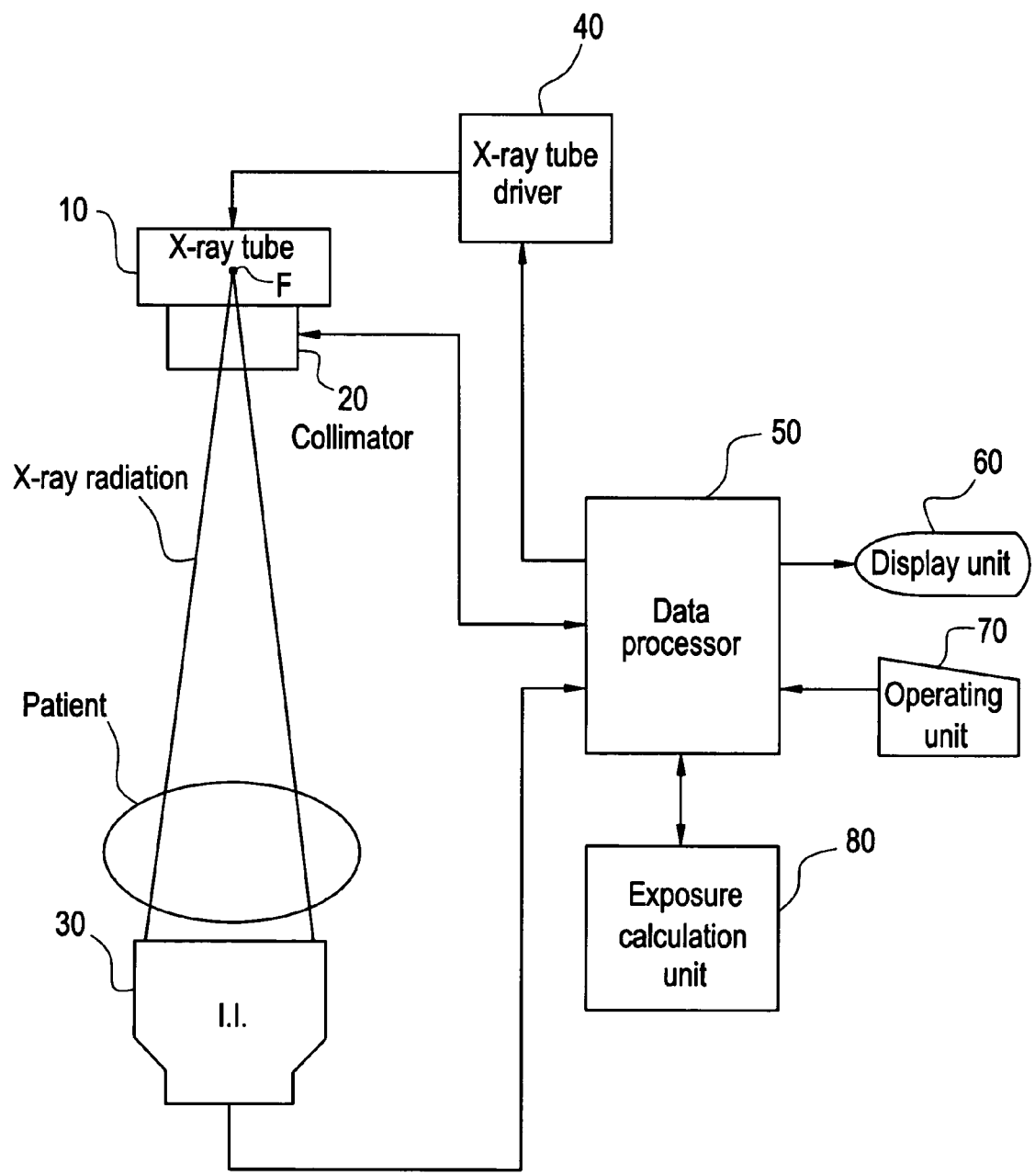
FIG. 1 is a block diagram of a radiography system.

Referring to drawings, the best mode for implementing the present invention will be described below. Noted is that the present invention shall not be limited to the best mode for implementing the present invention. FIG. 1 is a block diagram showing a radiography system. The radiography system is an example of the best mode for implementing the present invention. The configuration of the radiography system provides an example of a radiography system in which the present invention is implemented in the best mode. Actions to be performed in the radiography system provide an example of an exposure calculation method in which the present invention is implemented in the best mode.

As shown in FIG. 1, the radiography system includes an X-ray tube 10. X-rays generated from the focal spot F in the X-ray tube 10 are irradiated to a patient P via a collimator 20. The transmitted X-rays fall on the incidence surface of an image intensifier 30. Hereinafter, the image intensifier 30 shall be called the I.I. 30.

The X-ray tube 10 is driven by an X-ray tube driver 40. The X-ray tube driver 40 causes a tube voltage and a tube current to develop at or flows through the X-ray tube 10 so that the X-ray tube will generate X-rays. The X-ray tube driver 40 is controlled by a data processor 50. The data processor 50 is realized with, for example, a computer.

The data processor 50 controls the collimator 20 so as to adjust an X-ray field. The collimator 20 includes blades whose positions are variable. By changing the positions of the blades, the X-ray field can be varied. A detector incorporated in the collimator 20 detects the positions of the blades and feeds the detected positions back to the data processor 50. The collimator 20 will be described later.

The data processor 50 receives an X-ray detection signal from the I.I. 30, and constructs an image based on the input signal. The image is a fluoroscopic image of the patient P visualized with X-rays. The fluoroscopic image is displayed on a display unit 60 included in the data processor 50 and utilized for diagnosis.

The data processor 50 includes an operating unit 70. The operating unit 70 and display unit 60 provide a user interface, whereby a user can operate the radiography system interactively.

The data processor 50 includes an exposure calculation unit 80. The exposure calculation unit 80 is realized with, for example, a computer. The exposure calculation unit 80 may be incorporated in the data processor 50. The exposure calculation unit 80 calculates an exposure, which the patient P receives, on the basis of data received from the data processor 50, and transmits the result of the calculation to the data processor 50. The data processor 50 controls radiography according to the calculated exposure value. The foregoing components started with the X-ray tube 10 and ended with the operating unit 70 constitute an example of an imaging means included in the present invention. The exposure calculation unit 80 serves as an example of a detecting means included in the present invention.

Figure 2:
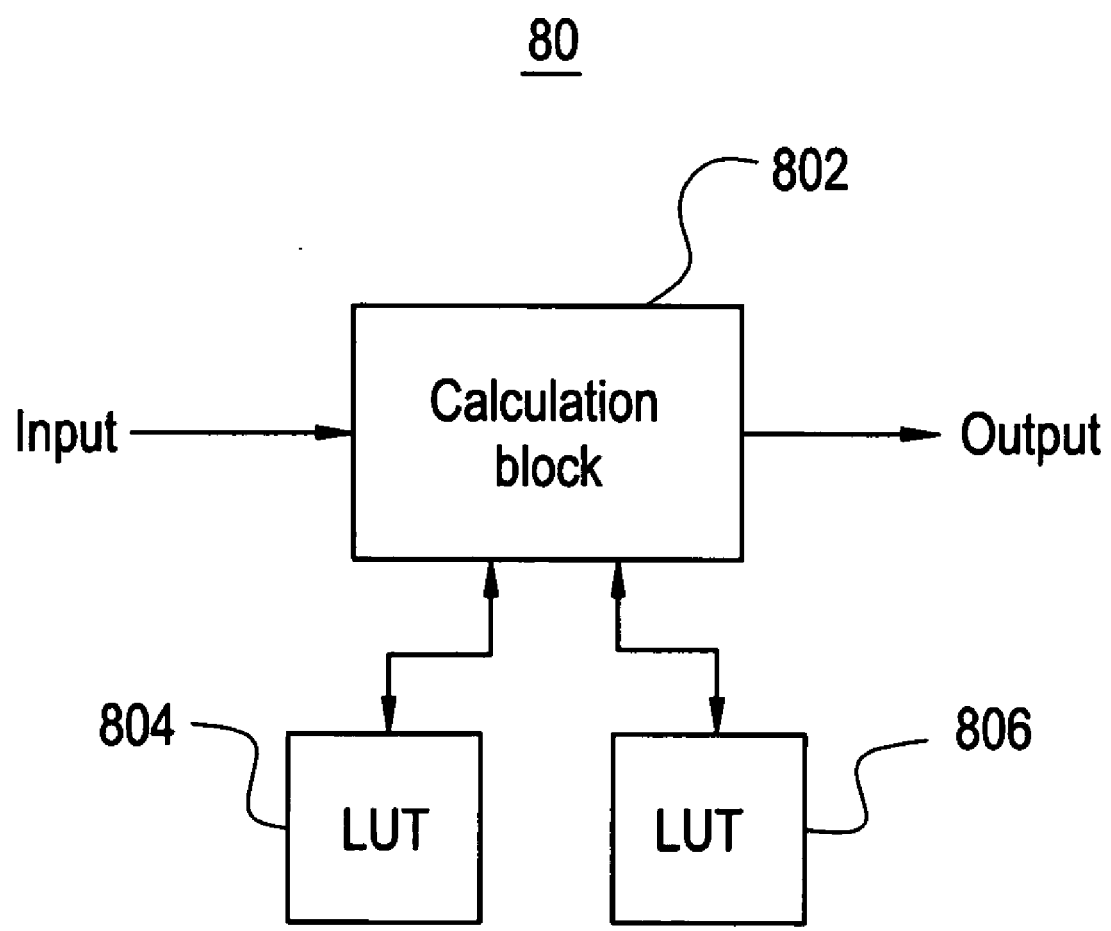
FIG. 2 is a block diagram of an exposure calculation unit.

FIG. 2 is a block diagram showing the exposure calculation unit 80. As illustrated, the exposure calculation unit 80 comprises a calculation block 802 and lookup tables 804 and 806. The calculation block 802 references the lookup tables 804 and 806 according to data received from the data processor 50, and calculates an exposure. The calculation of an exposure will be described later.

The calculation block 802 serves as an example of a calculating means included in the present invention. The lookup table 804 serves as an example of a first lookup table included in the present invention. The lookup table 806 serves as a second lookup table included therein.

Figure 3:
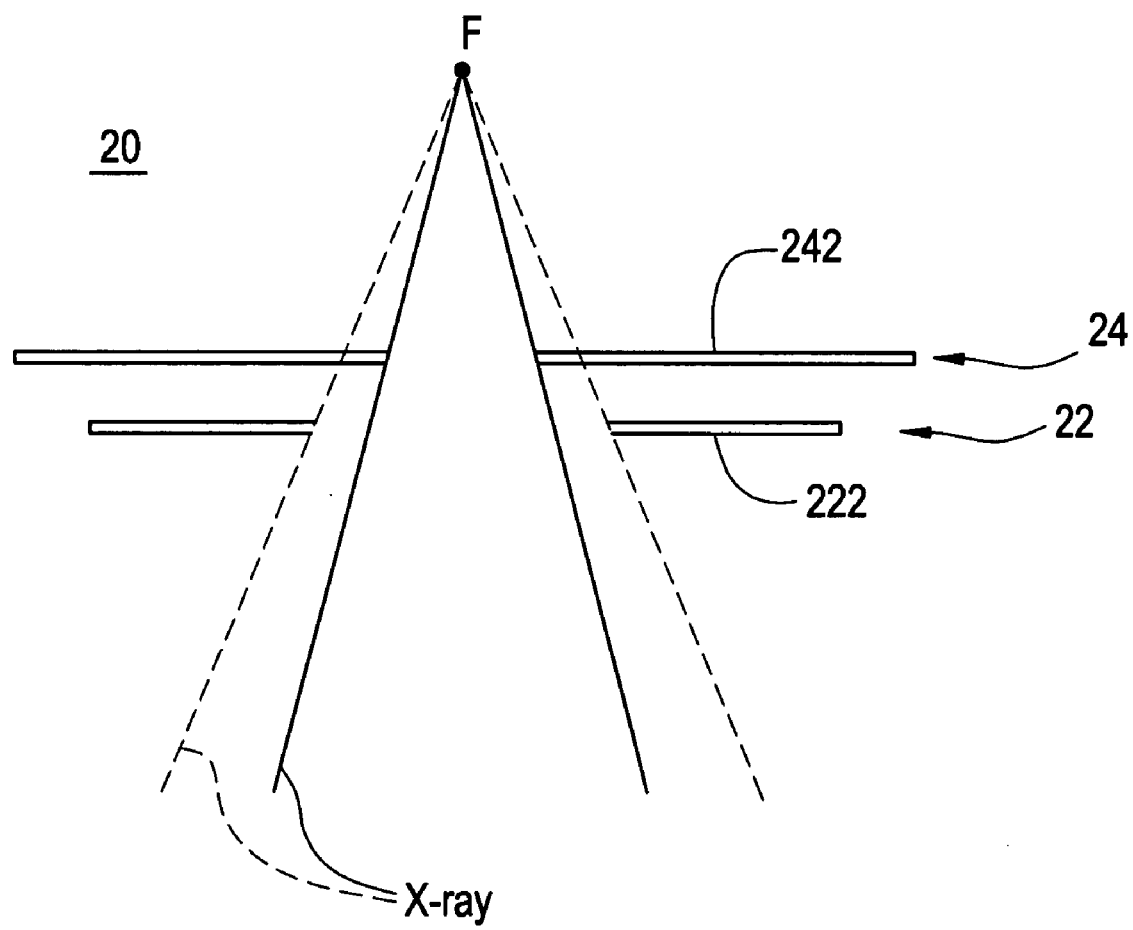
FIG. 3 shows the structure of a collimator.
Figure 4:
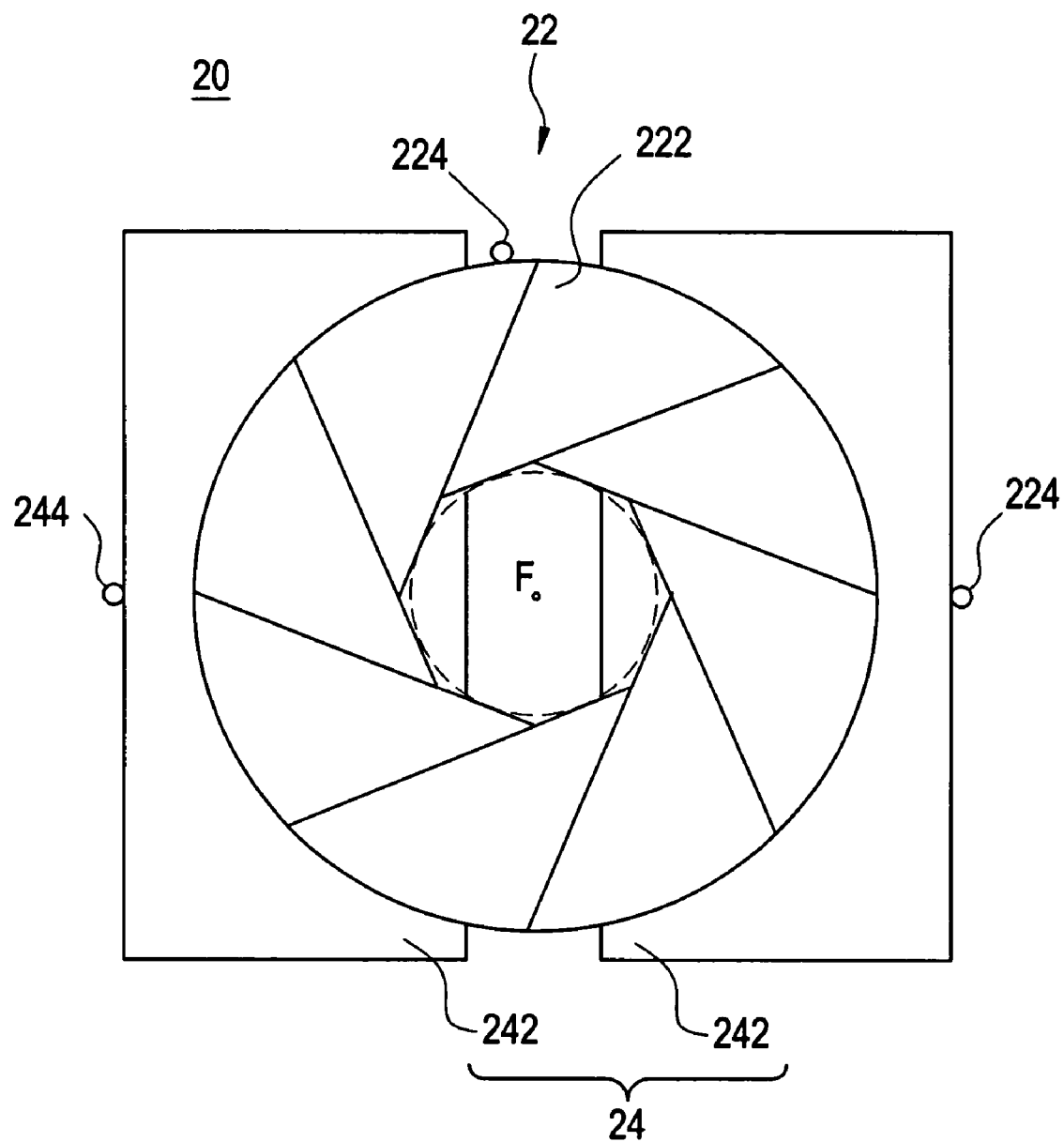
FIG. 4 shows the structure of the collimator.

The collimator 20 will be described below. FIG. 3 and FIG. 4 illustratively show the structure of the collimator 20. FIG. 3 is a side view of the collimator 20, and FIG. 4 is a plan view thereof seen from a side opposite to a side facing the focal spot F of X-rays. As illustrated, the collimator 20 comprises an iris diaphragm 22 and a shutter 24.

Incidentally, the collimator 20 may be devoid of the shutter 24 but may include the iris diaphragm 22 alone. Hereinafter, a description will be made on the assumption that the collimator 20 comprises the iris diaphragm 22 and shutter 24. The same will apply to a collimator having the iris diaphragm 22 alone.

The iris diaphragm 22 comprises, for example, eight blades 222. The blades 222 are made of an X-ray absorbent material, for example, lead (Pb) or tungsten (W). The eight blades 222 overlap to form an octagonal window in the center. The size of the window is variable by moving the eight blades 222 simultaneously. The window is, as indicated with dashed lines, approximated to an inscribed circle.

The blades 222 are driven by an actuator that is not shown, and displaced. The positions of the blades 222 are detected by a position detector 224, and fed back to the data processor 50.

The shutter 24 comprises, for example, two blades 242. The blades 242 are also made of an X-ray absorbent material. The two blades 242 are assembled to have their parallel sides opposed to each other. The spacing between the opposed sides of the two blades 242 can be varied by simultaneously moving the two blades 242 in mutually opposite directions. The blades 242 are driven by an actuator that is not shown, and displaced. The positions of the blades 242 are detected by a position detector 244 and fed back to the data processor 50.

The calculation of an exposure will be described below. To begin with, the lookup tables employed in the calculation of an exposure will be described. The relationship of correspondence between the values of a tube voltage and the values of a dose rate measured in advance is recorded in the lookup table 804. The relationship of correspondence between the values of the tube voltage and the values of the dose rate is defined based on the dose rate values actually measured using a dosimeter.

Specifically, the dosimeter is mounted on the incidence surface of the I.I. 30 when the patient P is absent. The dosimeter is used to measure the dose rate with the tube voltage set to a plurality of values. Incidentally, the tube current is retained at a certain value of, for example, 1 mA. Consequently, the relationship of correspondence between the values of the tube voltage and the values of the dose rate is determined, for example, as described in FIG. 5. The measurement is performed in the course of calibration of the X-ray tube 10 during manufacture of the radiography system.

The actually measured values are fitted to a quadratic function provided by the following quadratic expression:

$$\text{Doserate} = A\,(kV)^2 + B(kV) + C \quad (1)$$

Coefficients A, B, and C are determined through the fitting to the quadratic function, and a relational expression providing the correspondence between the tube voltage and the dose rate is determined. The relational expression is used to calculate the values of the dose rate associated with the various values of the tube voltage. The relationship of correspondence between the values of the tube voltage and the values of the dose rate is recorded in the form of a table in the lookup table.

The relationship of correspondence between the values each indicating the positions of the blades included in the collimator 20 and the values of the area of the X-ray field which are measured or calculated in advance is recorded in the lookup table 806. The relationship of correspondence between the values indicating the positions of the blades included in the collimator 20 and the values of the area of the X-ray field is determined based on actually measured values and values calculated using the actually measured values.

When the patient P is absent, a lead scale is mounted on the incidence surface of the I.I. 30. The sizes of projection images expressing the windows of the collimator 20 are measured with the positions of the plurality of bladed varied diversely. The sizes of the projection images determine the area of the X-ray field.

As for the iris diaphragm 22, the projection image of the window thereof is, as shown in FIG. 6, circular. The radius r of the circle is measured. As for the shutter 24, the projection image of the window thereof is, as shown in FIG. 7, shaped like a band. The half width d of the band is measured.

Consequently, for example, as shown in FIG. 8 and FIG. 9, the values of the radius r and half width d of the projection images are actually measured relative to the different positions of the blades in order to determine the relationship of correspondence between the values each indicating the positions of the blades and the values of the radius r or half width d. However, the values each indicating the positions of the blades are count values provided by the position detector associated with the iris diaphragm or shutter. The measurement is performed in the course of calibration of the collimator 20 during manufacture of the radiography system.

The measured values are fitted into a linear function provided by the following linear expression:

$$r=D(\text{count})+F$$

$$d=D'(\text{count})+F' \qquad (2)$$

Coefficients D, D', F, and F' are determined through the fitting to the linear function, and a relational expression providing the correspondence between the value indicating the positions of the blades and the area of the X-ray field is determined. The relational expression is used to calculate the radius r or half width d with the positions of the blades varied diversely.

Figure 10:
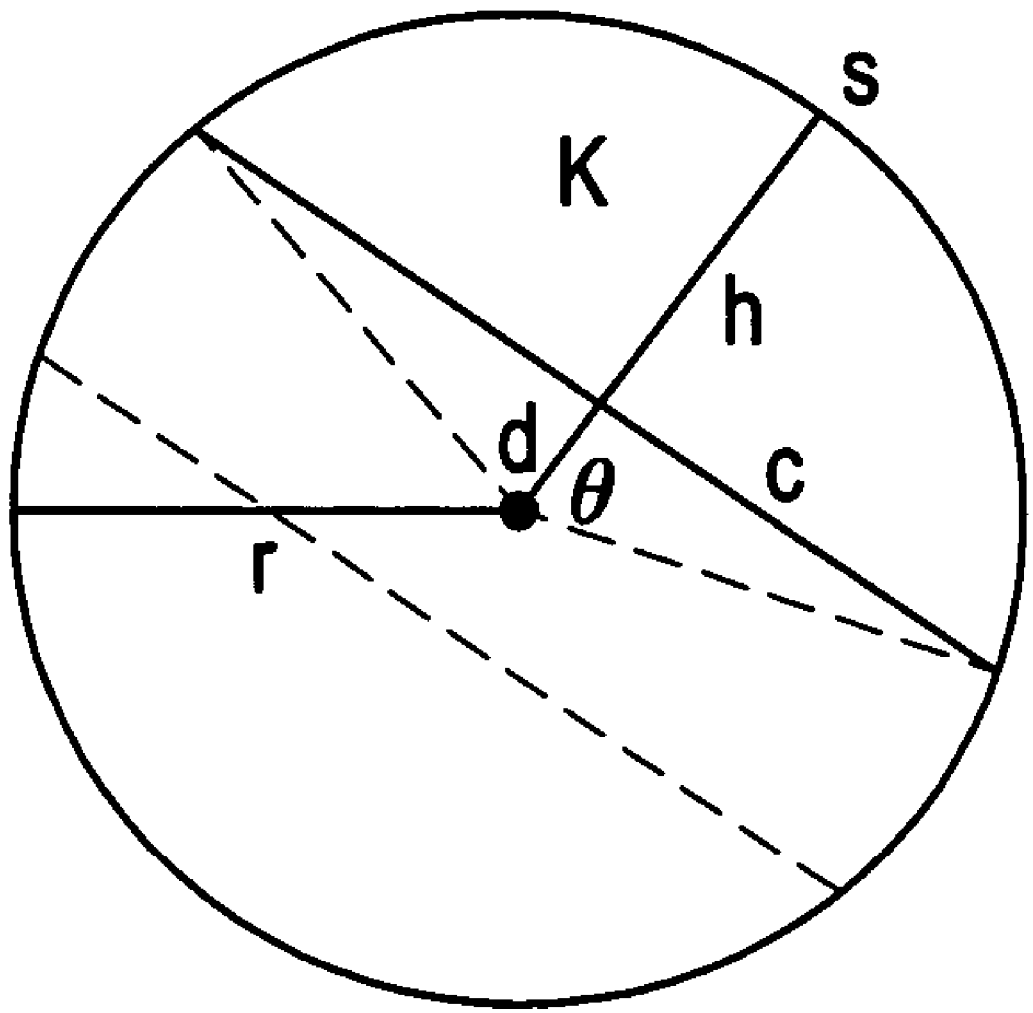
FIG. 10 is en explanatory diagram concerning calculation of the area of an X-ray field.

Once the radius r and half width d are known, the area of the X-ray field can be calculated based on the radius r and half width d. The calculation of the area of the X-ray field will be described in conjunction with FIG. 10. As shown in FIG. 10, when the radius r and half width d are known, the area of the X-ray field is calculated by subtracting the double of the area K of the portion of the circle, which has the radius r, defined with a chord c from the area of the circle having the radius r.

$$\text{AREA}=\pi r^2-2K \qquad (3)$$

The area K of the circle portion is calculated by subtracting the area of an isosceles triangle, of which base has a length c and of which vertical angle is the same as the vertical angle θ of a sector, from the area of the sector having the vertical angle θ. The vertical angle θ is provided as follows:

$$\theta=2\text{arc }\cos(d/r) \qquad (4)$$

The isosceles triangle has a height d, and the length c of the base of the isosceles triangle is provided as follows:

$$c=2r\,\sin(\theta/2) \qquad (5)$$

The length s of the arc of the circle portion is provided as follows:

$$s=r\theta \qquad (6)$$

Consequently, the area K of the circle portion is provided as follows:

$$K=r^2(\theta-\sin\,\theta)/2 \qquad (7)$$

The expression (7) is assigned to the expression (3), whereby the area of the X-ray field is provided as follows:

$$\text{AREA}=r^2(\pi-\theta+\sin\,\theta) \qquad (8)$$

When the collimator 20 includes the iris diaphragm 22 alone, the area of the X-ray field is provided as the expression (3) devoid of the second term.

The calculation of the area according to the expression (8) is performed relative to the various values of the radius r and half width d alike. Eventually, the tables presenting the relationship of correlation between the values each indicating the positions of the blades and the values of the area of the X-ray field are created. The tables are recorded in the lookup table 806.

Figure 11:
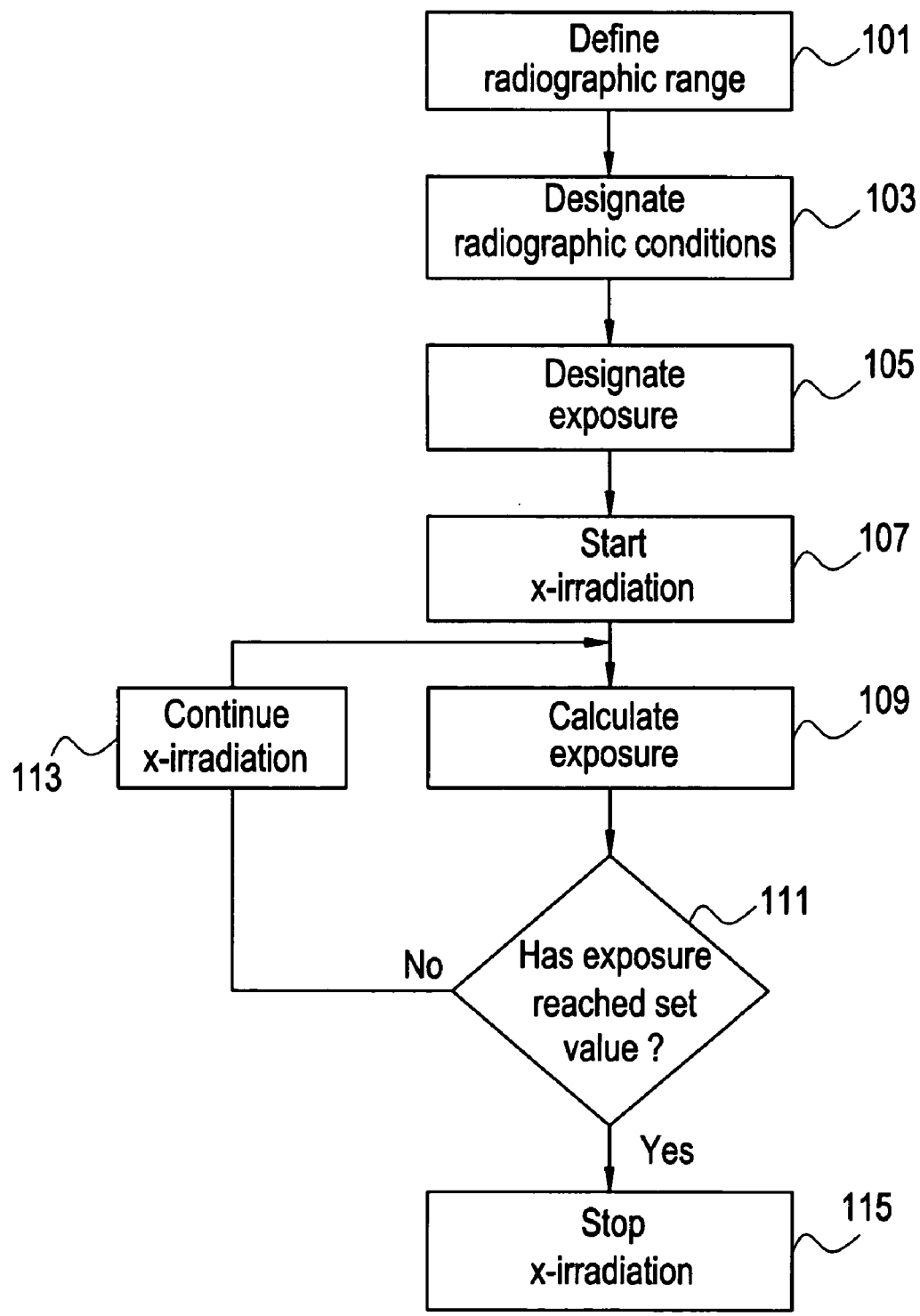
FIG. 11 is a flowchart describing radiography.

Actions to be performed in the radiography system will be described. FIG. 11 is a flowchart describing the actions. As described in the drawing, at step 101, a radiographic range is defined. A user defines the radiographic range using the operating unit 70. At step 103, radiographic conditions are designated. The user designates the radiographic conditions using the operating unit 70. Thus, the tube voltage and tube current are determined.

Thereafter, at step 105, an exposure is designated. The user designates the exposure using the operating unit 70. Thus, a desired value is designated as the exposure by which X-rays are irradiated to the patient P during radiography. At the next step 107, X-irradiation is started. When the user presses an irradiation button included in the operating unit 70, the X-irradiation is started.

Thereafter, at step 109, an exposure is calculated. The calculation block 802 included in the exposure calculation unit 80 calculates an exposure. The calculation block 802 calculates an exposure on the basis of the tube voltage, tube current, and X-irradiation time received from the data processor 50 and the information on the positions of the blades included in the collimator 20.

Specifically, the value of the dose rate associated with the value of the tube voltage is retrieved from the lookup table 804. The value of the area of the X-ray field associated with the information on the positions of the blades is retrieved from the lookup table 806. These pieces of information and the values of the tube current (mA) and X-irradiation time (sec) are used to calculate an exposure according to the following expression:

$$\text{DAP}=\text{DOSERATE}*\text{AREA}*\text{tube current}*\text{irradiation time} \qquad (9)$$

Consequently, the exposure of the patient P, that is, a dose area product (DAP) is calculated. The values of the dose rate and the area of the X-ray field employed in the calculation are the values measured on the incidence surface of the I.I. 30. Nevertheless, the dose area product calculated using these values can be regarded as a dose area product approximate to the exposure on the skin of the patient P. This is because although the dose rate is inversely proportional to the square of the distance from the focal spot F, since the area of the X-ray field is proportional to the square of the distance from the focal spot F, the product of the dose rate by the area of the X-ray field has nothing to do with the distance from the focal spot F.

Thereafter, at step 111, whether the exposure has reached a set value is judged. The judgment is made by the data processor 50. If the exposure has not reached the set value, X-irradiation is continued, at step 113. At step 109, the exposure is calculated. The exposure increases with the passage of the X-irradiation time and therefore duly reaches the set value. At step 115, X-irradiation is stopped. X-irradiation is automatically stopped by the data processor 50. Consequently, the exposure the patient P receives during radiography is adjusted as the user intends.

Many widely different embodiments of the invention may be configured without departing from the spirit and the scope of the present invention. It should be understood that the present invention is not limited to the specific embodiments described in the specification, except as defined in the appended claims.

What is claimed is:

1. A radiography system including an imaging device for imaging a patient by utilizing X-rays and a detecting unit for detecting an exposure the patient receives during radiography, wherein said detecting unit comprises:

a first lookup table in which a plurality of values of a dose rate are recorded in association with a plurality of values of a tube voltage of an X-ray tube;

a position detector configured to determine a value of a plurality of positions of a plurality of blades of a collimator that limits a range of X-ray radiation;

a second lookup table in which a plurality of values of an area of an X-ray field are recorded in association with a plurality of values including the value indicating the positions of the blades;

an operating unit configured to receive a tube current of said X-ray tube and a pre-determined value of the tube voltage; and a calculating device for retrieving one of the values of the dose rate which is associated with the pre-determined value of the tube voltage from said first lookup table, retrieving one of the values of the area of the X-ray field which is associated with a value indicating the positions of the blades included in said collimator from said second lookup table, and calculating a product of the dose rate, the area of the X-ray field, the tube current of said X-ray tube, and an X-irradiation time.

2. A radiography system according to claim 1, wherein said first lookup table is created through calibration of said X-ray tube performed using a dosimeter.

3. A radiography system according to claim 2, wherein said second lookup table is created through calibration of said collimator including measurement of the area of the X-ray field.

4. A radiography system according to claim 1, wherein the relationship of correspondence between the values indicating the positions of blades constituting each of an iris diaphragm and a shutter included in said collimator and the values of the area of the X-ray field is recorded in said second lookup table.

* * * * *